US008529501B2

(12) United States Patent
Wach et al.

(10) Patent No.: US 8,529,501 B2
(45) Date of Patent: Sep. 10, 2013

(54) ONE TIME USE BREASTPUMP ASSEMBLY

(75) Inventors: Joseph Wach, Ingleside, IL (US); Paul Avanzino, Crystal Lake, IL (US); Ryan Bauer, Fox River Grove, IL (US)

(73) Assignee: Medela Holding AG, Baar (CH)

( * ) Notice: Subject to any disclaimer, the term of this patent is extended or adjusted under 35 U.S.C. 154(b) by 496 days.

(21) Appl. No.: 12/794,317

(22) Filed: Jun. 4, 2010

(65) Prior Publication Data
US 2011/0301532 A1 Dec. 8, 2011

(51) Int. Cl.
*A61M 1/06* (2006.01)

(52) U.S. Cl.
USPC ............... 604/74; 604/73; 604/75; 604/76; 604/119; 604/131

(58) Field of Classification Search
USPC ............... 604/73, 74, 75, 119, 131, 76
See application file for complete search history.

(56) References Cited

U.S. PATENT DOCUMENTS

| 1,751,591 | A | * | 3/1930 | McCloskey | 251/208 |
|---|---|---|---|---|---|
| 2,016,200 | A | | 10/1935 | Howard | |
| 2,040,356 | A | | 5/1936 | Butcher | |
| 2,903,025 | A | * | 9/1959 | Richards | 141/217 |
| 3,259,154 | A | * | 7/1966 | Scherer | 141/209 |
| 3,445,032 | A | * | 5/1969 | Hansen et al. | 220/89.2 |
| 3,450,314 | A | * | 6/1969 | Gross | 222/402.24 |
| 4,137,955 | A | * | 2/1979 | Carlson | 141/349 |
| 4,522,623 | A | * | 6/1985 | Lauterjung | 604/319 |
| 4,543,980 | A | | 10/1985 | Van der Sanden | |
| 4,673,388 | A | * | 6/1987 | Schlensog et al. | 604/74 |
| 4,759,747 | A | * | 7/1988 | Aida et al. | 604/74 |
| 4,772,262 | A | | 9/1988 | Grant et al. | |
| 4,798,301 | A | | 1/1989 | Bullock et al. | |
| 4,877,146 | A | * | 10/1989 | Harris | 220/746 |
| 4,883,464 | A | * | 11/1989 | Morifuki | 604/74 |
| 4,886,494 | A | * | 12/1989 | Morifuji | 604/74 |
| 4,929,229 | A | * | 5/1990 | Larsson | 604/74 |
| 5,131,625 | A | | 7/1992 | Hacker et al. | |
| 5,238,655 | A | * | 8/1993 | Laible et al. | 604/405 |
| 5,308,321 | A | | 5/1994 | Castro | |
| 5,400,920 | A | * | 3/1995 | Barnhart | 222/1 |
| 5,571,084 | A | * | 11/1996 | Palmer | 604/74 |
| 5,775,528 | A | | 7/1998 | Wohlgemuth et al. | |

(Continued)

FOREIGN PATENT DOCUMENTS

| GB | 550187 | 12/1942 |
|---|---|---|
| JP | 01-240455 | 9/1989 |
| JP | 2002-302133 | 10/2002 |

OTHER PUBLICATIONS

International Search Report and Written Opinion for International Application No. PCT/US2011/039033, mailed Sep. 27, 2011.

*Primary Examiner* — Manuel A. Mendez
*Assistant Examiner* — Scott Medway
(74) *Attorney, Agent, or Firm* — McDonnell Boehnen Hulbert & Berghoff LLP

(57) ABSTRACT

A breastpump assembly is disclosed. The breastpump assembly includes a breast shield within which a woman's breast is received, a conduit structure communicating with the breast shield, a container for collecting milk, and a valve mechanism closing the breastpump assembly from ambient air when initially provided to a user, the valve mechanism being opened to allow ambient air to pass into the breastpump assembly through removal of the container, so as to substantially disable the breastpump.

11 Claims, 3 Drawing Sheets

(56) References Cited

U.S. PATENT DOCUMENTS

| | | | |
|---|---|---|---|
| 5,902,267 A * | 5/1999 | Medo | 604/74 |
| 5,918,854 A | 7/1999 | Barrash et al. | |
| 5,941,847 A | 8/1999 | Huber et al. | |
| 5,954,690 A * | 9/1999 | Larsson | 604/74 |
| 5,971,952 A * | 10/1999 | Medo | 604/74 |
| 6,042,560 A * | 3/2000 | Niederberger | 604/74 |
| 6,090,065 A * | 7/2000 | Giles | 604/74 |
| 6,110,140 A | 8/2000 | Silver | |
| 6,112,923 A | 9/2000 | Ma | |
| 6,270,474 B1 * | 8/2001 | Nuesch | 604/74 |
| 6,358,226 B1 * | 3/2002 | Ryan | 604/74 |
| 6,383,163 B1 | 5/2002 | Kelly et al. | |
| 6,461,324 B1 | 10/2002 | Schlensog | |
| 6,500,143 B2 * | 12/2002 | Suh | 604/73 |
| 6,517,513 B1 * | 2/2003 | Covington et al. | 604/74 |
| 6,585,686 B2 * | 7/2003 | Cloud | 604/74 |
| 6,676,610 B2 * | 1/2004 | Morton et al. | 600/573 |
| 6,712,785 B2 * | 3/2004 | Morton et al. | 604/74 |
| 6,749,582 B2 | 6/2004 | Britto et al. | |
| 6,875,184 B2 * | 4/2005 | Morton et al. | 600/573 |
| 6,884,229 B2 | 4/2005 | Renz | |
| 6,974,439 B1 | 12/2005 | McKendry | |
| 6,981,950 B2 * | 1/2006 | Morton et al. | 600/573 |
| 7,166,087 B2 | 1/2007 | Silver et al. | |
| 7,237,570 B2 * | 7/2007 | Gamard et al. | 137/613 |
| 7,267,662 B1 * | 9/2007 | Kirchner | 604/74 |
| 7,445,130 B2 | 11/2008 | Bosl et al. | |
| 7,503,910 B2 * | 3/2009 | Adahan | 604/319 |
| 7,559,915 B2 * | 7/2009 | Dao et al. | 604/74 |
| 7,666,162 B2 * | 2/2010 | Renz et al. | 604/74 |
| 7,776,008 B2 * | 8/2010 | Renz et al. | 604/74 |
| 7,875,000 B2 * | 1/2011 | Krebs et al. | 604/73 |
| 7,878,373 B2 * | 2/2011 | Lindmayer | 222/153.13 |
| 8,002,514 B2 * | 8/2011 | Hagstrom et al. | 414/810 |
| 8,100,854 B2 * | 1/2012 | Vogelin et al. | 604/74 |
| 8,118,772 B2 * | 2/2012 | Dao et al. | 604/74 |
| 8,128,607 B2 * | 3/2012 | Hu et al. | 604/313 |
| 8,191,566 B2 * | 6/2012 | Donahue | 137/68.23 |
| 2001/0047148 A1 * | 11/2001 | Suh | 604/74 |
| 2002/0004642 A1 * | 1/2002 | Cloud | 604/74 |
| 2002/0032404 A1 * | 3/2002 | Silver | 604/74 |
| 2002/0189683 A1 * | 12/2002 | Danby et al. | 137/494 |
| 2003/0204164 A1 * | 10/2003 | Britto et al. | 604/74 |
| 2003/0230351 A1 | 12/2003 | Renz | |
| 2004/0087898 A1 | 5/2004 | Weniger | |
| 2004/0215138 A1 * | 10/2004 | Greter et al. | 604/74 |
| 2005/0015045 A1 * | 1/2005 | Tashiro et al. | 604/74 |
| 2005/0067441 A1 * | 3/2005 | Alley | 222/547 |
| 2005/0154349 A1 | 7/2005 | Renz et al. | |
| 2005/0196441 A1 * | 9/2005 | Dvorsky et al. | 424/466 |
| 2006/0148380 A1 | 7/2006 | Rousso et al. | |
| 2007/0016152 A1 * | 1/2007 | Karpowicz et al. | 604/326 |
| 2007/0173756 A1 | 7/2007 | Krebs et al. | |
| 2007/0262042 A1 * | 11/2007 | Pareja | 215/17 |
| 2008/0009815 A1 * | 1/2008 | Grabenkort et al. | 604/346 |
| 2008/0045888 A1 | 2/2008 | Edwards et al. | |
| 2008/0208116 A1 * | 8/2008 | Dao et al. | 604/74 |
| 2009/0084752 A1 * | 4/2009 | Coulson | 215/311 |
| 2009/0099511 A1 * | 4/2009 | Sutrina et al. | 604/74 |
| 2010/0042021 A1 * | 2/2010 | Hu et al. | 601/6 |
| 2010/0158751 A1 * | 6/2010 | Friderich et al. | 422/27 |

* cited by examiner

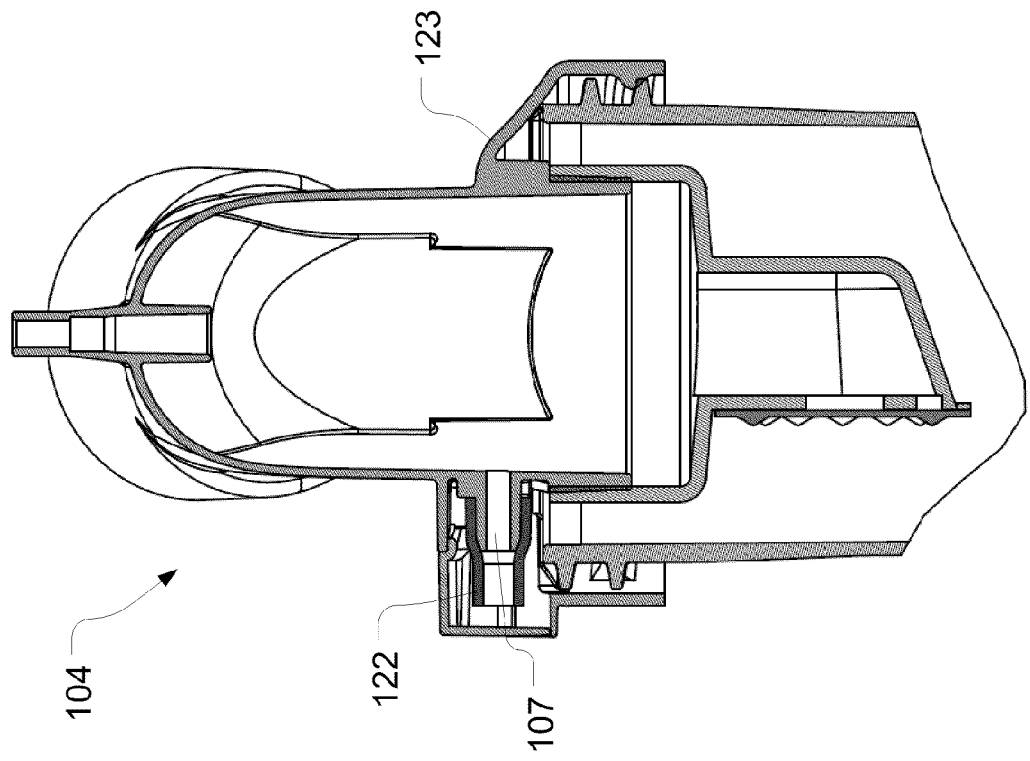
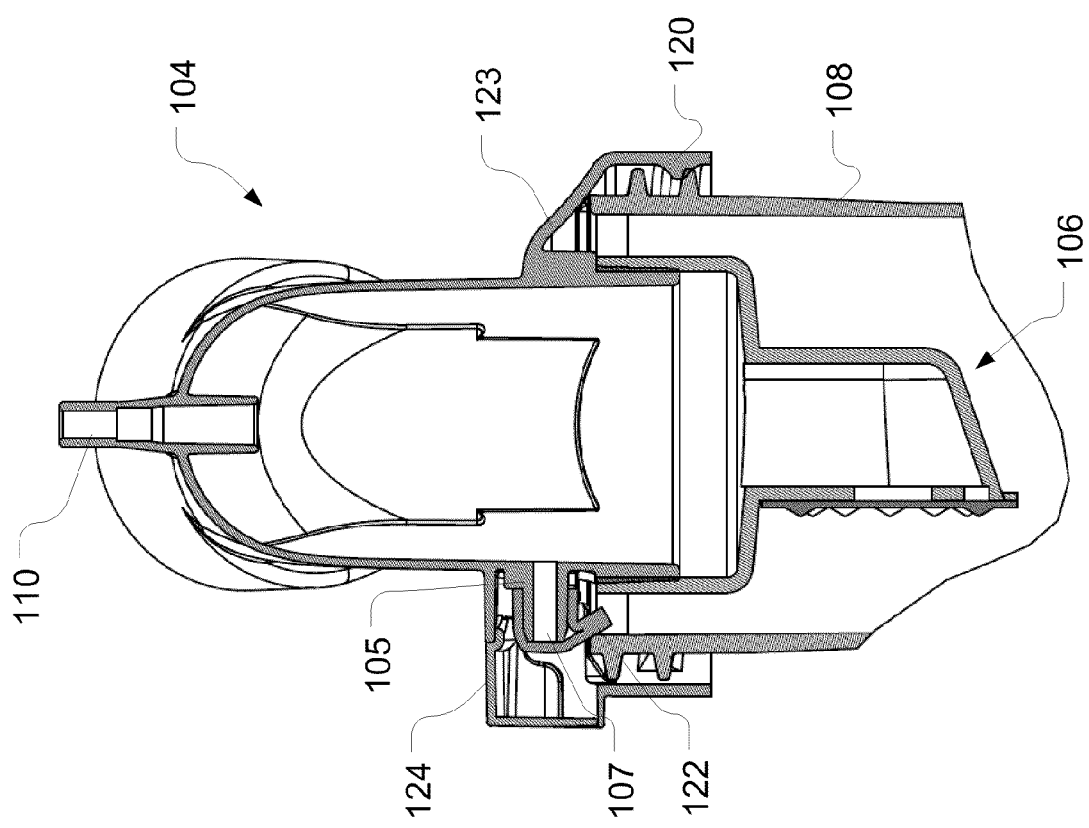

ONE TIME USE BREASTPUMP ASSEMBLY

FIELD OF THE INVENTION

This invention relates to breastpumps for drawing breastmilk, and particularly to a breastpump assembly having a mechanism that prevents the breastpump from re-use, e.g., a disposable breastpump assembly.

BACKGROUND OF THE INVENTION

Current breastpumping technologies require a pumping kit that functions as the milk collection interface to the mother from the vacuum generating breastpump. Currently, these kits are designed to be re-useable in that they can be disassembled, cleaned, and used for multiple pumping sessions.

In the hospital, mothers are provided with sterile kits for their personal use. Once a mother uses a kit, it is no longer sterile and it is generally incumbent upon the mother to clean the kit for subsequent uses. Cleaning typically involves hand washing, boiling, microsteaming, or placing in the dishwasher. In some cases the hospital may be involved in the cleaning process during the mother's stay, such as when autoclaving is employed. Hospitals may also provide sinks and cleaning agents for the mother's convenience. Cleaning practices vary widely from hospital to hospital and from mother to mother. Hospitals frequently provide mothers with disposable sterile bottles to pump into, but the kit, which most of the milk must pass through, is no longer sterile after the first use.

Improperly cleaned kits can easily become contaminated with undesirable microbes, mold, mildew, dirt, etc. For some hospitals and mothers it is desirable to have a freshly sterilized kit available for each pumping session, especially for hospitals with contaminated water supplies, and for high-risk infant patients such as those staying in the Neonatal Intensive Care Unit (NICU). In order to ensure that the pumping kits can only be used in their sterile form, it is desirable to provide a kit that ceases to function after the kit is used for the first time.

Separately, there are pumping mothers that would simply desire a hygienic, ready-to-use kit that would suffice for a single use where convenience outweighs the cost benefits of cleaning and using a re-usable kit. Cleaning facilities are not always available or practical.

Accordingly, it would be desirable to provide a breastpump assembly that only works during the first pumping session that the mother employs the assembly. Preferably, the kit (breastpump assembly and perhaps tubing and other collateral optional elements) would employ tamper resistant features that prevent the mother from bypassing the function that limits the single use. Additionally, the kit would preferably be able to be supplied in a sterile form as desired for hospital markets. Elements of the kit would not require the durability features required to meet the rigors of re-use conditions such as exposure to steam, boiling, and autoclaving.

SUMMARY OF THE INVENTION

The present application discloses a disposable breast pump assembly including a breast shield having a first end for placement on a breast and a second end for connection to a collection container, a conduit structure communicating with the breast shield, the conduit structure being in connection with a vacuum source, and a valve mechanism connected to the second end of the breast shield, the valve mechanism disabling the vacuum function after the disposable breast pump assembly has been used. The valve mechanism may simply be an opening which is initially closed, but then opened by removal of some part of the breastpump assembly.

BRIEF DESCRIPTION OF THE DRAWINGS

These and other features and advantages of the present invention will be further understood and appreciated when considered in relation to the following detailed description of embodiments of the invention, taken in conjunction with the drawings, in which:

FIG. 2 is a rear view partly in section of the breastpump assembly of FIG. 1 (assembled) with the valve mechanism in the functional (closed) position;

FIG. 3 is a similar view of the breastpump assembly shown in FIG. 2 with the valve mechanism in the non-functional (open) position.

DETAILED DESCRIPTION OF EMBODIMENTS OF THE INVENTION

Figure 1:
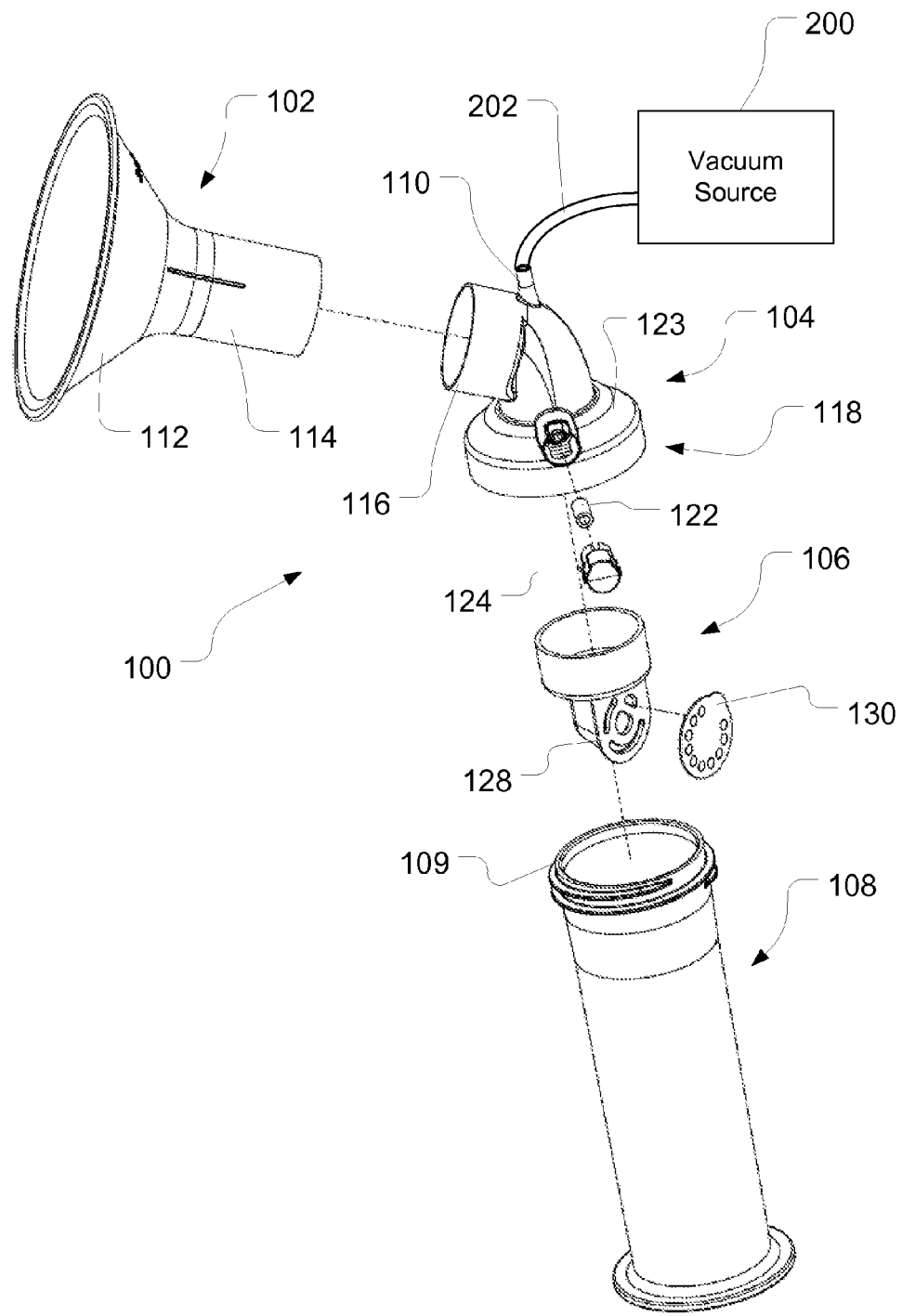
FIG. 1 is an exploded view of an embodiment of a breastpump assembly according to certain aspects of the present invention.

One embodiment of the invention is shown in a breastpump assembly of FIGS. 1 through 3. This type of breastpump assembly is simply illustrative, and not intended to be limiting of the invention.

The breastpump assembly 100 includes a breast shield 102, for receiving a breast. The breast shield 102 is attached to a conduit structure 104. The conduit structure 104 may include a connection port 110 that attaches to a vacuum source 200 through a tube or hose 202. The vacuum source 200 may be an electric pump, such as the pumps disclosed in U.S. Pat. Nos. 6,547,756 or 6,257,847, each of which are incorporated herein by reference in their entirety, and can be referred to for details of the breastpumping equipment in general. Alternatively, the breastpump assembly 100 may be used with a manual pump, which is also well known in the art. The nature of the source of vacuum is not significant to the invention.

The conduit structure 104 transmits vacuum generated in the vacuum source 200 to the breast shield 102, and moves expressed breastmilk from the breast shield 102 through a check valve assembly 106 to an attached container 108. The container 108 may include a lip 109. The container 108, such as a standard baby bottle, communicates with ambient air when the breastpump assembly 100 is in use, as by a pathway provided via the threaded engagement or a vent hole (not shown) in a cap-part 123 of the conduit structure 104. Again, these common details can be gleaned from art well known in the breastpumping business.

The breast shield 102 has a generally funnel shaped portion 112 at a first end, and is sized for being received onto a breast. The breast shield 102 extends into a sleeve 114 downstream from the funnel shaped portion 112 at a second end. The sleeve, or nipple tunnel, 114 conducts expressed milk into the conduit structure 104. For purposes of the instant invention, the shape of the breast shield 102 and its formation with the conduit structure 104 are generally incidental to the invention; again, the particular arrangement and details of these elements is in no way limiting.

The conduit structure 104 is attachable to the breast shield 102 through a shield mount 116 sized and shaped to receive the sleeve 114. The conduit structure 104 may also include an orifice 105 which may be closed to air ingress to maintain a vacuum within the conduit structure. The conduit structure 104 is generally a housing (base) that interconnects and permits fluid communication between parts of the breastpump assembly 100 that includes not only milk flow, but also pressure (e.g., vacuum) communication. Here, the conduit structure 104 connects to the sleeve 114, by way of the shield mount 116 at an upstream end, and terminates with a check valve assembly 106 at a container attachment end 118. The container attachment end 118 may include threads 120 (FIGS. 2 and 3) or any suitable mechanism for releasable attachment to container 108, which may be in the form of a milk bottle or the like.

Provided in the conduit structure 104 is a valve mechanism 122 for closing the pathway 107 in the orifice 105. The valve mechanism 122 may comprise a one-time valve, pop-up valve, or flap valve for example. The valve mechanism 122 here is mechanically attached to the orifice 105. It should be understood that the valve mechanism 122 may take alternate forms, such as any type of closure that prevents ambient air from entering the conduit structure 104, but is then opened by removal of some part of the breastpump assembly 100. This valve mechanism 122 comprises a tube being folded upon itself in a first, pinched position, to close the valve and thereby the orifice 105. The valve mechanism 122 is held in the first, pinched position by the lip 109 of the container 108. As will be understood, the valve mechanism 122 may be located elsewhere to communicate with the conduit structure 104, and may be held in the first position by another structure, which when moved (as for cleaning, emptying, etc.), opens the valve or opening.

The valve mechanism 122 is surrounded by a valve cover 124, which is part of the cap-part 123. The valve cover 124 communicates with ambient air, at least when the valve mechanism 122 is open. In the first, pinched position, the valve mechanism 122 closes an air pathway 107 located in the orifice 105. The valve mechanism 122 is made of a flexible material, such as thermoplastic elastomer, rubber, or silicone rubber, for example.

The check valve assembly 106 includes a rigid wall or base 128 and a thin flexible membrane 130 (or flap), made of rubber or silicone rubber; such is detailed in U.S. Pat. No. 4,929,229, incorporated herein by reference. The wall 128 is circular (disk-like) in shape, and can either be removably engaged or integrated with the conduit structure 104. The wall 128 includes a plurality of openings.

In operation, the breastpump assembly 100 is provided in the condition shown in FIG. 2. The container 108 collects milk during a pumping session. Typically, the container 108 may be a bottle or a bag. During pumping, the conduit structure 104 is closed to air ingress from the container 108 under a negative pressure applied within the conduit structure 104 in a first position where the valve mechanism 122 is closed and held in a pinched position by the container 108, as shown in FIG. 2. When the valve mechanism 122 is in the closed, pinched position, the pathway 107 in the orifice 105 is closed, and a vacuum is maintainable in the breastpump assembly 100.

After pumping, the container 108 is separated from the rest of the breastpump assembly 100 to be placed in storage for later delivery to the infant. When the container 108 is removed from the conduit structure 104, however, the valve mechanism 122 automatically opens into a second, uncompressed position within the valve cover 124, since it is no longer pinched by the container 108, as shown in FIG. 3. In this second position, the pathway 107 is opened and ambient air may pass into the breastpump assembly 100. Alternatively, removal of a portion of the breastpump assembly, such as the check valve or tubing, may free the valve mechanism 122 from the first pinched position into the second position.

When a mother attempts to attach the container 108 or a new container (not shown) to the conduit structure 104, the valve mechanism 122 remains in the open position, thereby allowing air ingress from the container when a container is reattached to the conduit structure 104. Vacuum is leaked out of (not maintained in) the breastpump assembly 100 through the valve mechanism 122, rendering the assembly substantially or completely non-functional. Thus, the breastpump assembly 100 is substantially disabled and cannot be re-used once the container 108 is removed.

Figure 4:
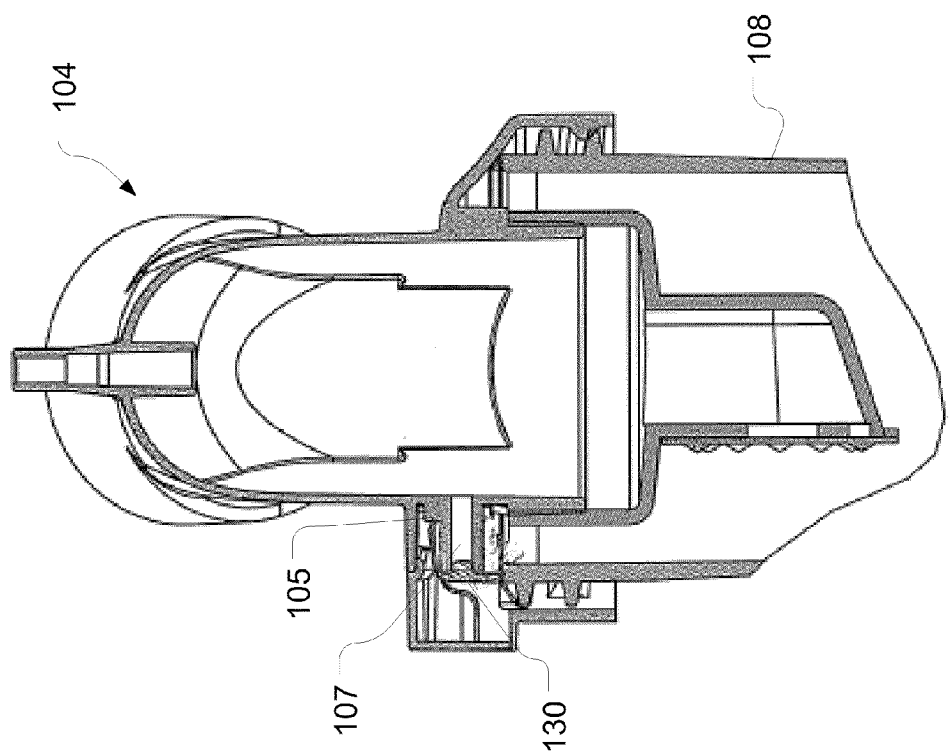
FIG. 4 is a similar view of the breastpump assembly as shown in FIG. 2 showing an alternate embodiment of the valve mechanism.

In yet another embodiment, a breakaway tab or collar may be used to free the container 108 from the conduit structure, thereby preventing the container 108 from being reattached to the conduit structure 104. This might be a frangible member or a stopper 130, as shown in FIG. 4, which covers the pathway 107 in orifice 105 in the first, closed position, and which is attached to the container 108. Rotation or removal of the container 108 mechanically moves the frangible member or stopper 130 from the closed position.

In yet another embodiment, the breastpump assembly 100 may be comprised of materials that cannot withstand heat and/or moisture commonly seen in cleaning processes. Such materials may include polyethylene or polystyrene, for example. These materials would be designed to warp or otherwise degrade under heat. In yet another embodiment, the breastpump assembly 100 may include parts that fatigue and cease to function upon repeated use.

Thus, while the invention has been described herein with relation to certain embodiments and applications, those with skill in this art will recognize changes, modifications, alterations and the like which still come within the spirit of the inventive concept, and such are intended to be included within the scope of the invention as expressed in the following claims.

What is claimed is:

1. A disposable breast pump assembly comprising:
 a breast shield having a first end for placement on a breast and a second end for connection to a collection container;
 a conduit structure communicating with the breast shield, the conduit structure being in connection with a vacuum source to provide a vacuum function to the breast pump assembly; and
 a valve mechanism connected to the second end of the breast shield and located remote from the vacuum source, wherein the valve mechanism opens to allow ambient air ingress into the conduit structure, thereby disabling the vacuum function after the disposable breast pump assembly has been used and rendering the breast pump assembly substantially or completely non-functional.

2. A breastpump comprising:
 a breast shield within which a woman's breast is received;
 a conduit structure communicating with said breast shield, said conduit structure including an interior passageway for conveying milk and air;
 a container for collecting milk;
 a mechanism connecting said container to said conduit structure; and
 a valve mechanism communicating with ambient air disposed at least partially within said interior passageway of the conduit structure;
 wherein said conduit structure is closed to air ingress from ambient air when a negative pressure from a vacuum source is applied within said conduit structure in a first position where said valve mechanism is closed; and wherein said valve mechanism is opened when said container is detached from said conduit structure, thereby allowing ambient air ingress into the conduit structure when said container is reattached to said conduit structure, so as to substantially disable the breastpump from generating a sufficient negative pressure to convey milk or air within said conduit structure.

3. The breastpump of claim 2, wherein said valve mechanism is a flexible member interposed and compressed between said container and a part of said conduit structure when in said first position and thereby closing an orifice to said conduit structure for air ingress, said flexible member moving to a second position when said container is detached and opening said orifice, said flexible member further remaining in said second position when said container is reattached.

4. The breastpump of claim 3 wherein said valve mechanism is a tube, said tube being folded upon itself in said first position to thereby close said tube and said orifice, said tube being attached to said orifice.

5. The breastpump of claim 2 wherein said valve mechanism is a cover, said cover closing an opening to said conduit structure in said first position to thereby close said opening, said cover being attached to said container such that when said container is detached, said cover opens said opening.

6. A breastpump, comprising:
a breast shield within which a woman's breast is received;
a conduit structure communicating with said breast shield, said conduit structure including a pathway for conveying milk and air, said conduit structure being substantially closed to air ingress in a first condition when a vacuum is applied within said conduit structure;
a container for collecting milk;
a mechanism attaching said container to said conduit structure; and
a valve disposed between said conduit structure and said container, said valve being located in the pathway to ambient air, said valve being in an initial closed position when said container is first attached to said conduit structure, said valve being automatically opened when said container is detached from said conduit structure, thereby allowing air ingress through said pathway in the event that said container is reattached to said conduit structure, so as to substantially disable the breastpump from generating a sufficient vacuum to convey milk or air within said conduit structure.

7. A one-time use breastpump comprising:
a breastpump assembly including a breast shield within which a woman's breast is received, and conduit structure between said breast shield and container;
a container for expressed milk attached to the breastpump assembly; and
a valve mechanism closing said breastpump assembly from ambient air when initially provided to a user, said valve mechanism being opened to allow ambient air to pass into said breastpump assembly through detachment of said container, so as to substantially disable the breastpump and render the breastpump substantially or completely non-functional;
wherein said valve mechanism is a flexible member interposed and compressed between said container and a part of said conduit structure when in a first position and thereby closing an orifice to said conduit structure for air ingress, said flexible member moving to a second position when said container is detached and opening said orifice, said flexible member further remaining in said second position when said container is reattached.

8. A one-time use breastpump comprising:
a breastpump assembly including a breast shield within which a woman's breast is received, and conduit structure between said breast shield and said container;
a container for expressed milk attached to the breastpump assembly; and
a closure in an opening to said breastpump assembly, said closure preventing ingress of ambient air when the breastpump assembly is initially provided to a user, said closure being in mechanical connection to a part of said breastpump assembly and caused to open and thereby allow ambient air to pass into said breastpump assembly through detachment of said part from said breastpump assembly, so as to substantially disable the breastpump and render the breastpump assembly substantially or completely non-functional;
wherein said closure is a flexible member interposed and compressed between said container and a part of said conduit structure when in a first position and thereby closing an orifice to said conduit structure for air ingress, said flexible member moving to a second position when said container is detached and opening said orifice, said flexible member further remaining in said second position when said container is reattached.

9. A breastpump comprising:
a breast shield within which a woman's breast is received;
a conduit structure communicating with said breast shield, said conduit structure including an interior passageway for conveying milk and air;
a container for collecting milk;
a mechanism connecting said container to said conduit structure; and
a valve mechanism communicating with ambient air disposed at least partially within said interior passageway of the conduit structure;
wherein said conduit structure is closed to air ingress from ambient air when a negative pressure is applied from a vacuum source within said conduit structure in a first position where said valve mechanism is closed, wherein the vacuum source provides a vacuum function to the breastpump; and
wherein said valve mechanism is opened when a structure in direct communication with the valve mechanism is detached from the breastpump, thereby allowing ambient air ingress into the conduit structure when said structure is reattached to the breastpump, so as to substantially disable the breastpump so that the vacuum function cannot be re-enabled.

10. A one-time use breastpump comprising:
a breastpump assembly including a breast shield within which a woman's breast is received, and conduit structure between said breast shield and container;
a container for expressed milk attached to the breastpump assembly; and
a valve mechanism closing said breastpump assembly from ambient air when initially provided to a user, said valve mechanism being opened to allow ambient air to pass into said breastpump assembly through detachment of a portion of the breastpump assembly, so as to substantially disable the breastpump and render the breastpump substantially or completely non-functional;
wherein said valve mechanism is a flexible member interposed and compressed between said container and a part of said conduit structure when in a first position and thereby closing an orifice to said conduit structure for air ingress, said flexible member moving to a second position when said container is detached and opening said orifice, said flexible member further remaining in said second position when said container is reattached.

11. A breastpump comprising:
a breast shield within which a woman's breast is received;
a conduit structure communicating with said breast shield, said conduit structure including an interior passageway for conveying milk and air;
a container for collecting milk;
a mechanism connecting said container to said conduit structure; and
a valve mechanism communicating with ambient air disposed at least partially within said interior passageway of the conduit structure;
wherein said conduit structure is closed to air ingress from ambient air when a negative pressure from a vacuum source is applied within said conduit structure in a first position where said valve mechanism is closed, wherein the vacuum source provides a vacuum function to the breastpump; and
wherein said valve mechanism is opened when a part of the breastpump is detached from the breastpump, thereby allowing ambient air ingress into the conduit structure, so as to substantially disable the breastpump so that the vacuum function cannot be re-enabled.

* * * * *